(12) United States Patent
Kawai et al.

(10) Patent No.: US 12,171,202 B2
(45) Date of Patent: Dec. 24, 2024

(54) REARING APPARATUS

(71) Applicant: JTEKT CORPORATION, Kariya (JP)

(72) Inventors: Shigekazu Kawai, Osaka (JP); Yasuhiro Murata, Osaka (JP); Takashi Matsumoto, Osaka (JP); Takahito Watanabe, Tokushima (JP); Taro Mito, Tokushima (JP)

(73) Assignee: JTEKT CORPORATION, Kariya (JP)

( * ) Notice: Subject to any disclaimer, the term of this patent is extended or adjusted under 35 U.S.C. 154(b) by 37 days.

(21) Appl. No.: 17/907,228

(22) PCT Filed: Feb. 26, 2021

(86) PCT No.: PCT/JP2021/007465
§ 371 (c)(1),
(2) Date: Sep. 23, 2022

(87) PCT Pub. No.: WO2021/192820
PCT Pub. Date: Sep. 30, 2021

(65) Prior Publication Data
US 2023/0095722 A1 Mar. 30, 2023

(30) Foreign Application Priority Data
Mar. 24, 2020 (JP) .................. 2020-052445

(51) Int. Cl.
*A01K 67/033* (2006.01)
(52) U.S. Cl.
CPC ...... *A01K 67/033* (2013.01); *A01K 2227/706* (2013.01)

(58) Field of Classification Search
CPC ........... A01G 67/033; A01G 2227/706; A01K 67/033; A01K 2227/706
See application file for complete search history.

(56) References Cited

U.S. PATENT DOCUMENTS 4,319,371 A * 3/1982 Wiederrich .......... A01K 67/033
449/4
5,351,643 A * 10/1994 Hughes ................ A01K 67/033
119/6.5

(Continued)

FOREIGN PATENT DOCUMENTS

EP      3772276 A1 * 2/2021 .......... A01K 67/033
JP      10-191834 A    7/1998

(Continued)

OTHER PUBLICATIONS

International Search Report with English translation and Written Opinion mailed on Apr. 20, 2021 in PCT/JP2021/007465 filed on Feb. 26, 2021 (8 pages).

(Continued)

*Primary Examiner* — Monica L Perry
*Assistant Examiner* — Aaron M Rodziwicz
(74) *Attorney, Agent, or Firm* — Oblon, McClelland, Maier & Neustadt, L.L.P.

(57) ABSTRACT

A rearing apparatus for rearing an organism includes: a box-shaped rearing case; at least one perching member that is held in the rearing case and for perching the organism; and a separating member that is provided in the rearing case and that is movable along the perching member. The separating member is configured to separate the organism perched at the perching member from the perching member by the separating member moving along the perching member.

10 Claims, 7 Drawing Sheets

(56) References Cited

U.S. PATENT DOCUMENTS

| | | | |
|---|---|---|---|
| 6,561,125 B1 | 5/2003 | Lohsomboon | |
| 2006/0288942 A1* | 12/2006 | Miller | A01K 67/033 |
| | | | 119/6.7 |
| 2007/0218804 A1* | 9/2007 | Allan | A01K 47/00 |
| | | | 449/4 |
| 2017/0311612 A1* | 11/2017 | Leo | A21D 2/34 |
| 2017/0360014 A1* | 12/2017 | Hall | B65G 1/0492 |
| 2018/0049414 A1* | 2/2018 | Leo | C11C 1/10 |
| 2018/0049415 A1* | 2/2018 | Leo | A23K 20/163 |
| 2018/0049416 A1* | 2/2018 | Leo | A01K 67/033 |
| 2018/0049417 A1* | 2/2018 | Leo | A23K 20/174 |
| 2018/0049418 A1* | 2/2018 | Leo | A01K 67/033 |
| 2018/0055021 A1* | 3/2018 | Calis | A01K 67/033 |
| 2019/0075762 A1* | 3/2019 | Kapka | A01K 47/00 |
| 2019/0085279 A1* | 3/2019 | Leo | A23L 2/56 |
| 2019/0246591 A1* | 8/2019 | Leo | B01D 11/0296 |
| 2020/0288685 A1* | 9/2020 | Rood | A01K 1/03 |
| 2021/0352878 A1* | 11/2021 | Llecha Galiñanes | A01K 1/01 |
| 2022/0287284 A1* | 9/2022 | Martínez Escribano | B65D 43/0212 |

FOREIGN PATENT DOCUMENTS

| | | |
|---|---|---|
| JP | 3208272 U | 1/2017 |
| KR | 10-2018-0134172 A | 12/2018 |
| WO | WO-2017155419 A1 * 9/2017 | ............. A01K 47/00 |

OTHER PUBLICATIONS

Extended European Search Report issued on Dec. 1, 2023 in European Patent Application No. 21774508.2, 8 pages.

* cited by examiner

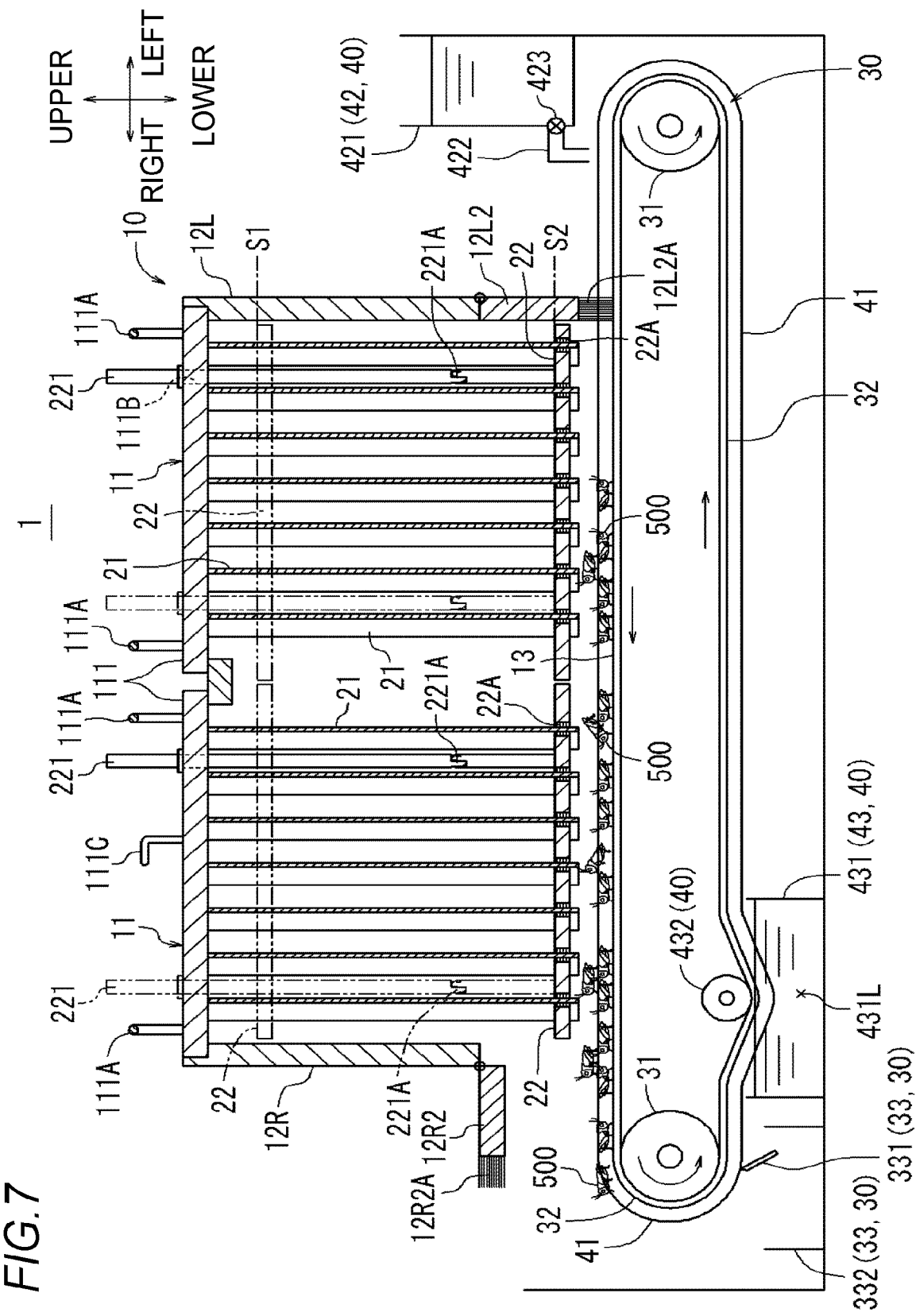

REARING APPARATUS

TECHNICAL FIELD

The present disclosure relates to a rearing apparatus used for rearing an organism.

BACKGROUND ART

In order to rear an organism in an environment suitable for growth, various objects are provided in a rearing container in which the organism is reared. The organism is, for example, an insect. For example, JPH10-191834A discloses a rearing apparatus for a cricket that rears a cricket in a rearing container having a cubic structure. Further, JPH10-191834A describes, for example, providing a container in which absorbent cotton containing water is placed in the rearing container in order to water the cricket, and providing a large number of lightly rolled newspapers in the rearing container such that the cricket can hide in a shadow. As described above, in the related art, the cricket has been reared and bred only manually, and it takes time and effort to manage hygiene. Therefore, it is not easy to rear the crickets at high density or to increase a rearing scale since it takes a large amount of time and effort.

In order to collect the cricket in the rearing apparatus according to JPH10-191834A, it takes time and effort to separate a variety of objects provided in the rearing container and the cricket. That is, in the rearing apparatus described in JPH10-191834A, the cricket may be hidden inside the large number of lightly rolled newspapers provided in the rearing container, or the cricket may cling to the rolled newspapers. Therefore, when the cricket is collected in the rearing apparatus described in JPH10-191834A, it takes a large amount of effort to check whether the cricket is hidden inside the rolled newspaper for each of the large number of rolled newspapers, and to separate the cricket clinging to the rolled newspaper from the newspaper. Due to the effect and time, in the rearing apparatus described in JPH10-191834A, it takes time and effort to collect the cricket.

SUMMARY OF INVENTION

The present disclosure provides a rearing apparatus capable of rearing an organism in an environment suitable for growth, and further facilitating collection of the reared organism.

According to a first aspect of the present disclosure, a rearing apparatus for rearing an organism includes: a box-shaped rearing case; at least one perching member that is held in the rearing case and that is capable of perching the organism; and a separating member that is provided in the rearing case and that is movable along the perching member. The separating member is configured to separate the organism perched at the perching member from the perching member by the separating member moving along the perching member.

According to a second aspect of the present disclosure, in the rearing apparatus of the above first aspect, the separating member may include a seal member that fills a gap between the separating member and the perching member.

According to a third aspect of the present disclosure, in the rearing apparatus of the above first or second aspect, the separating member may include a moving member configured to reciprocate between a rearing position at which the separating member is positioned when rearing the organism and a collection position at which the separating member is positioned when collecting the organism.

According to a fourth aspect of the present disclosure, in the rearing apparatus of the above third aspect, the moving member may be a rod-shaped member capable of being folded at the rearing position.

According to a fifth aspect of the present disclosure, in the rearing apparatus of any one of the above first to fourth aspects, the rearing apparatus may further include: a belt conveyor provided at a bottom portion of a space in the rearing case.

According to a sixth aspect of the present disclosure, in the rearing apparatus of the above fifth aspect, a belt of the belt conveyor may include a water supply member capable of retaining water inside the belt and capable of supplying the retained water to the organism.

According to the first aspect, the rearing apparatus includes a perching member and a separating member. The organism reared in the rearing case can move and perch at the perching member. In this way, the organism can perch at the perching member, so that the rearing apparatus can rear the organism in an environment more suitable for growth. By moving the separating member along the perching member, the organism perched at the perching member can be separated from the perching member. Accordingly, it is easier to collect the reared organism. Therefore, the rearing apparatus can rear an organism in an environment suitable for growth, and further facilitates collection of the reared organism.

According to the second aspect, the rearing apparatus includes a seal member that fills a gap between the separating member and the perching member. The seal member prevents the organism from passing through the gap between the separating member and the perching member. Therefore, by providing the seal member, the separating member is moved along the perching member. Accordingly, the organism perched at the perching member can be separated more reliably when being separated from the perching member.

According to the third aspect, the separating member includes a moving member configured to reciprocate between a rearing position at which the separating member is positioned when the organism is reared and a collection position at which the separating member is positioned when the organism is collected. By providing the moving member, it is easier to move the separating member along the perching member. Therefore, it is easier to separate the organism perched at the perching member from the perching member.

According to the fourth aspect, the moving member is a rod-shaped member capable of being folded at the rearing position. Accordingly, it is more reliable and easier to move the separating member. By folding the rod-shaped member, it is possible to prevent the moving member from straightly protruding from the rearing case and becoming bulky.

According to the fifth aspect, the rearing apparatus includes a belt conveyor provided at a bottom portion of a space in the rearing case. The belt conveyor can more easily discharge deposits (for example, excrement, shells, carcasses, and leftover food) deposited on the bottom portion of the space in the rearing case from the inside of the rearing case to the outside.

According to the sixth aspect, the rearing apparatus includes a water supply member capable of retaining water inside the belt of the belt conveyor and supplying the retained water to the organism. Accordingly, water can be supplied to the organism as long as the water supply member is used. Therefore, it is easy to apply water to the organism.

BRIEF DESCRIPTION OF DRAWINGS

FIG. 7 is an explanatory diagram showing the method for using the rearing apparatus according to the embodiment.

DESCRIPTION OF EMBODIMENTS

Figure 1:
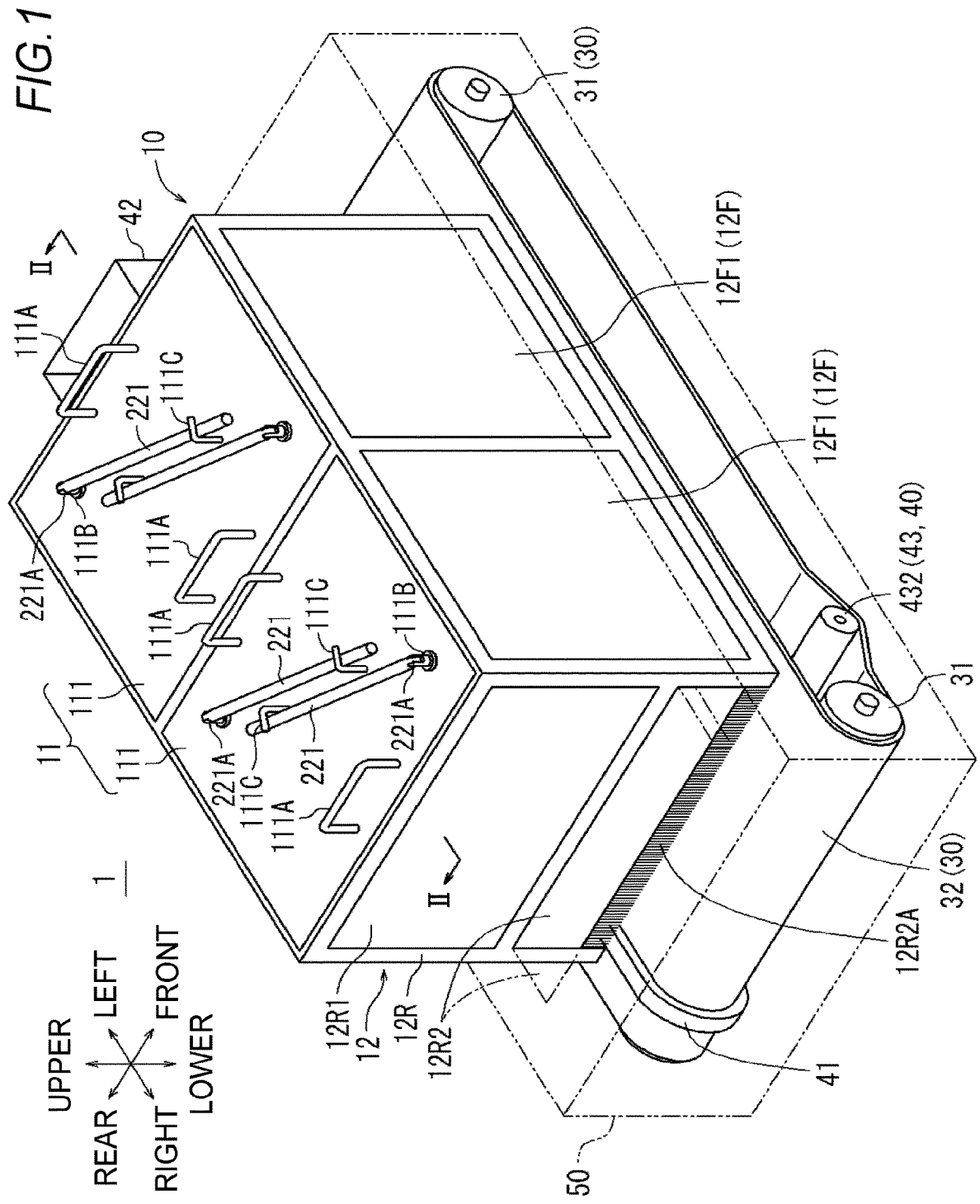
FIG. 1 is a schematic perspective view of a rearing apparatus according to an embodiment.

Hereinafter, a rearing apparatus 1 according to an embodiment of the present disclosure will be described with reference to the drawings. The rearing apparatus 1 according to the embodiment is a rearing apparatus used for rearing an organism. The organism to be reared is preferably an animal that can move on the ground, and further, from the viewpoint of a size of the animal, an insect that can move on the ground is particularly preferable. The rearing apparatus 1 can be a rearing apparatus for an insect. In the present embodiment, the organism to be reared is a cricket such as a gryllus bimaculatus or a house cricket, which is a type of insect, as an example of the organism, and is described as a "cricket 500" in the drawings and in the following description.

As shown in FIG. 1, the rearing apparatus 1 according to the embodiment includes a box-shaped rearing case 10 configured to rear an organism inside, a belt conveyor 30 provided at a bottom portion of the rearing case 10, a belt-shaped water supply band 41 wound around a belt 32 of the belt conveyor 30, and the like. In the drawings and the following description, a front-rear direction, a left-right direction, and an upper-lower direction all indicate the following directions. That is, the upper-lower direction indicates a vertical upward direction and a downward direction. As shown in FIG. 1, the front indicates a direction from a side where the water supply band 41 on the belt 32 is present to a side where the water supply band 41 is not present among directions crossing the belt 32 of the belt conveyor 30, and the rear indicates an opposite direction to the front. The left-right direction is a left-right direction defined with reference to the front-rear direction and the upper-lower direction.

[Configuration of Rearing Apparatus 1 According to Embodiment (FIGS. 1 to 6)]

Figure 2:
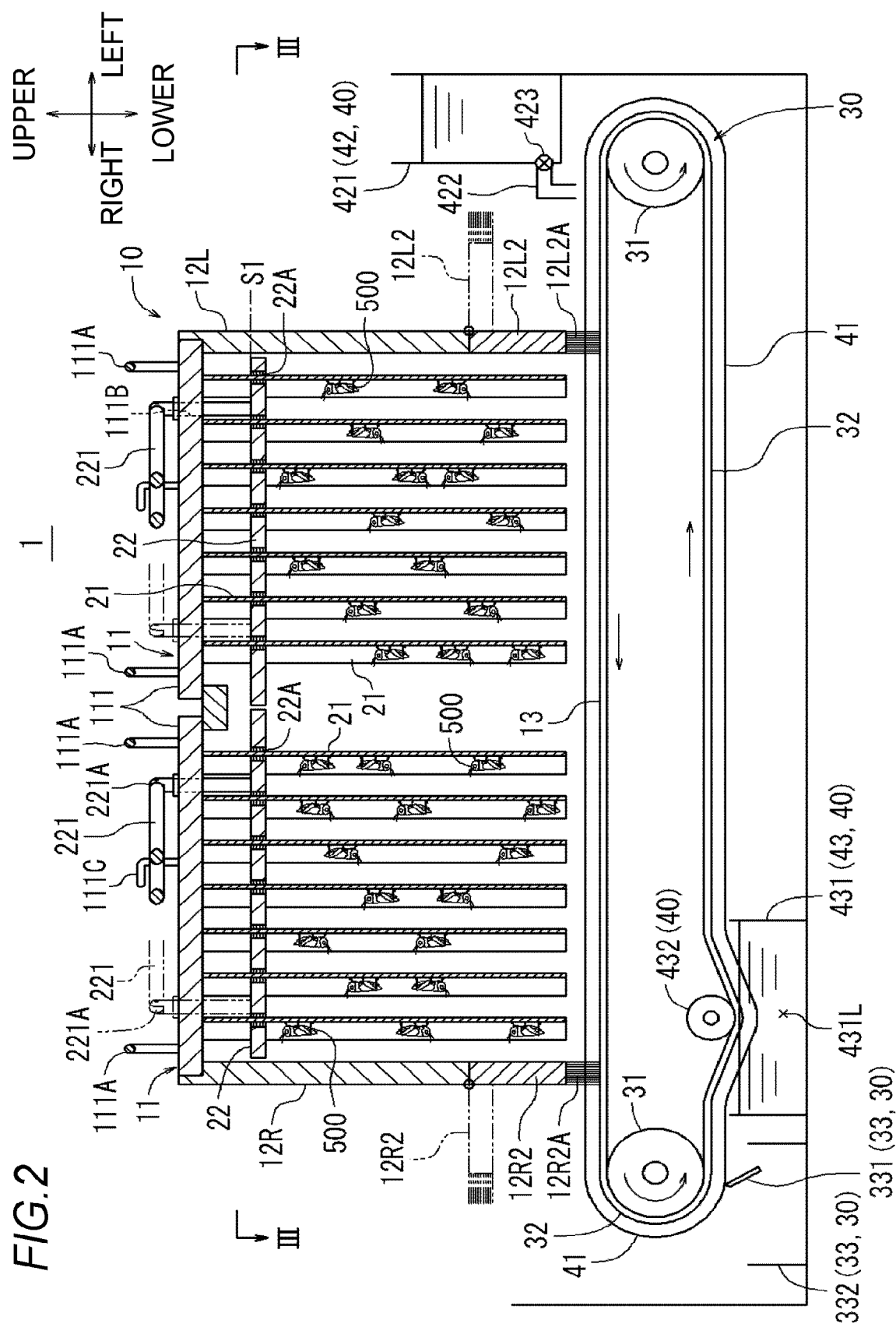
FIG. 2 is a cross-sectional view taken along a line II-II in FIG. 1.
Figure 3:
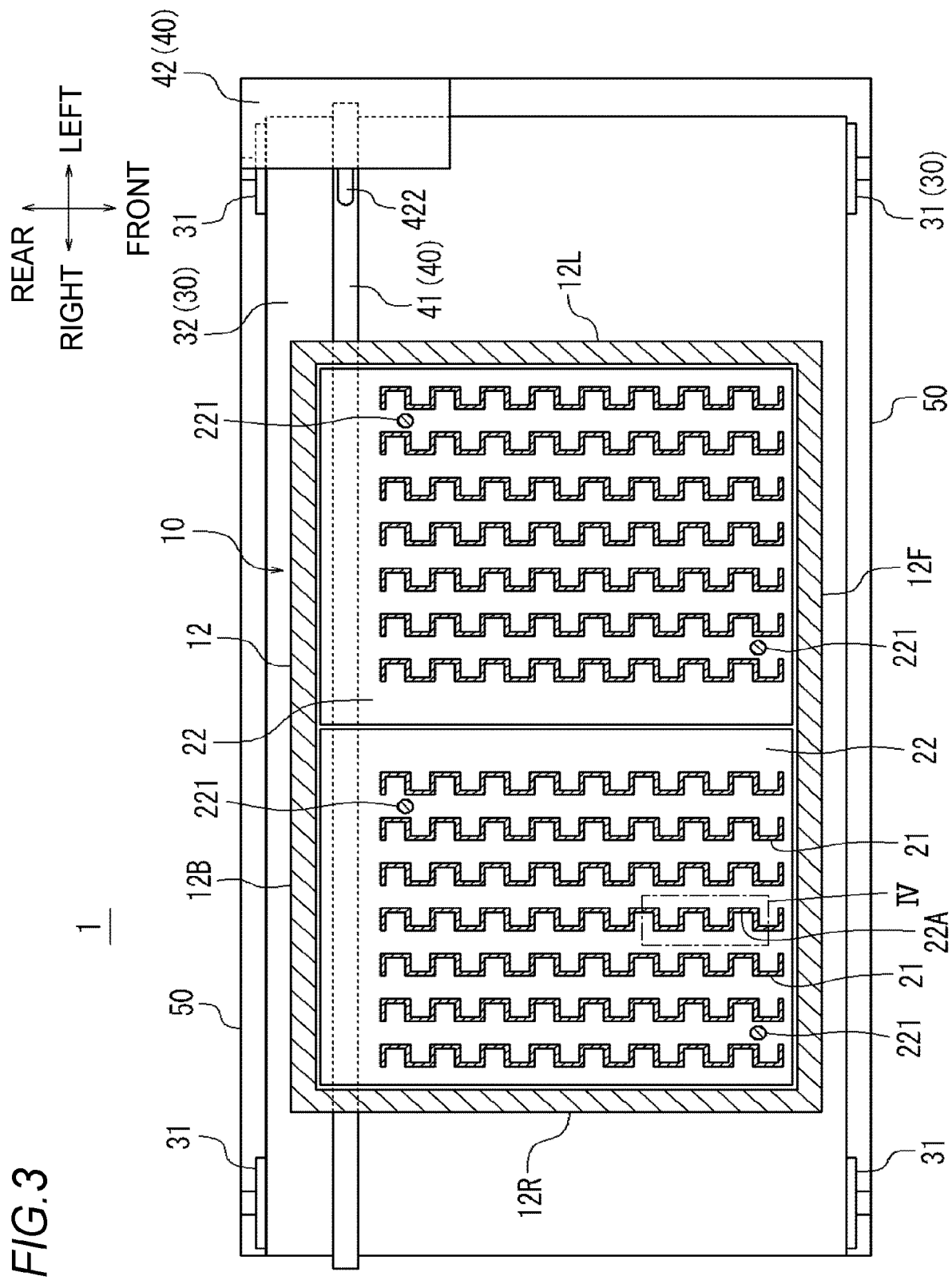
FIG. 3 is a cross-sectional view taken along a line in FIG. 2.
Figure 4:
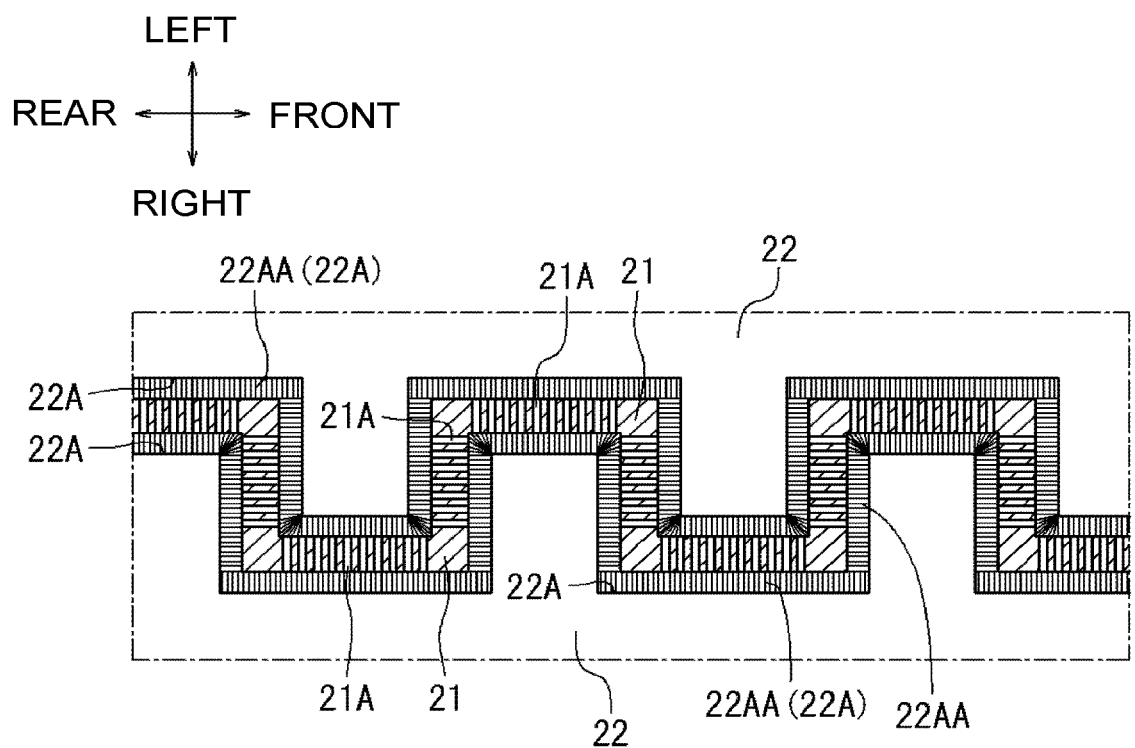
FIG. 4 is an enlarged view of a portion IV in FIG. 3.
Figure 5:
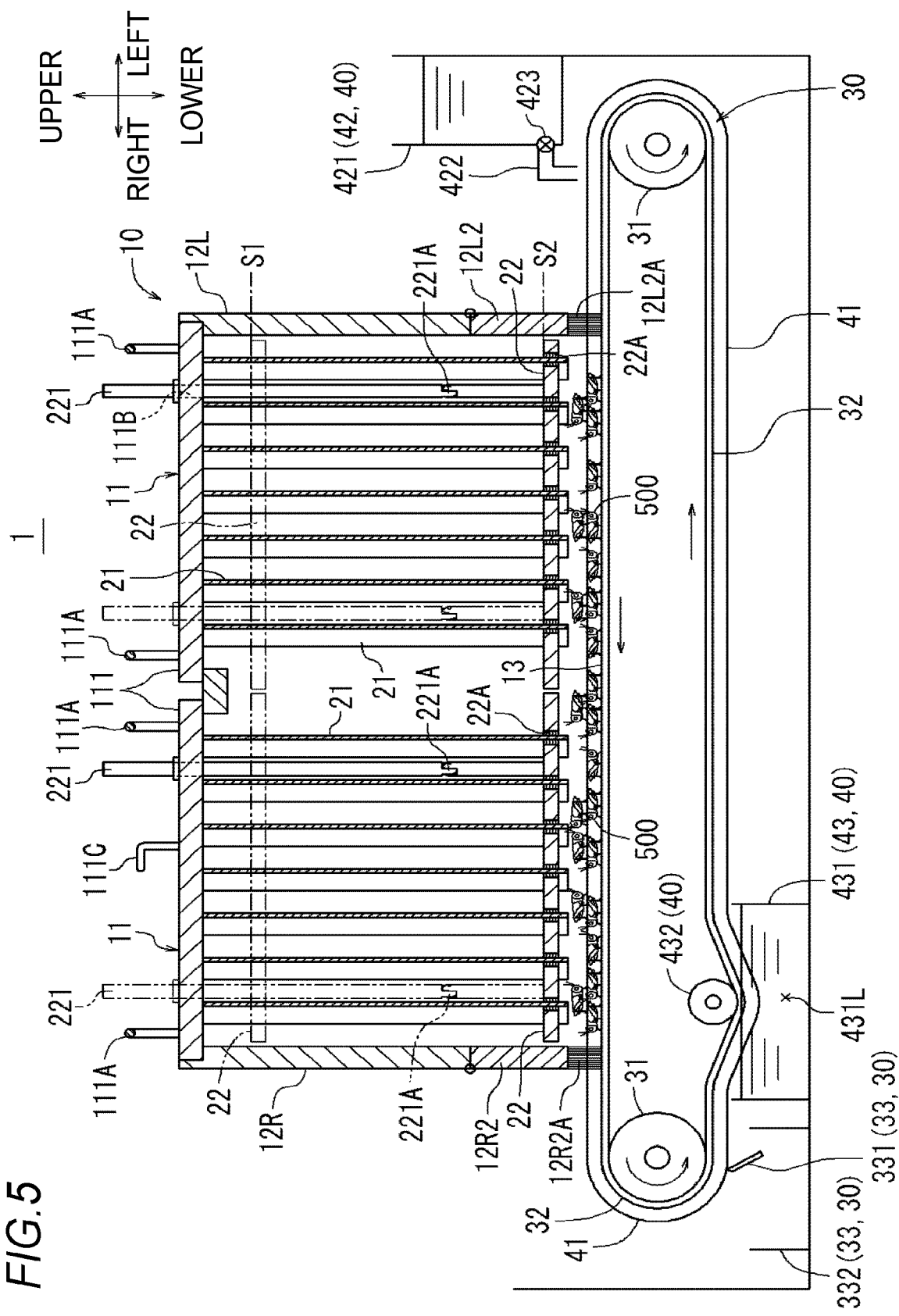
FIG. 5 is an explanatory diagram showing a method for using the rearing apparatus according to the embodiment.
Figure 6:
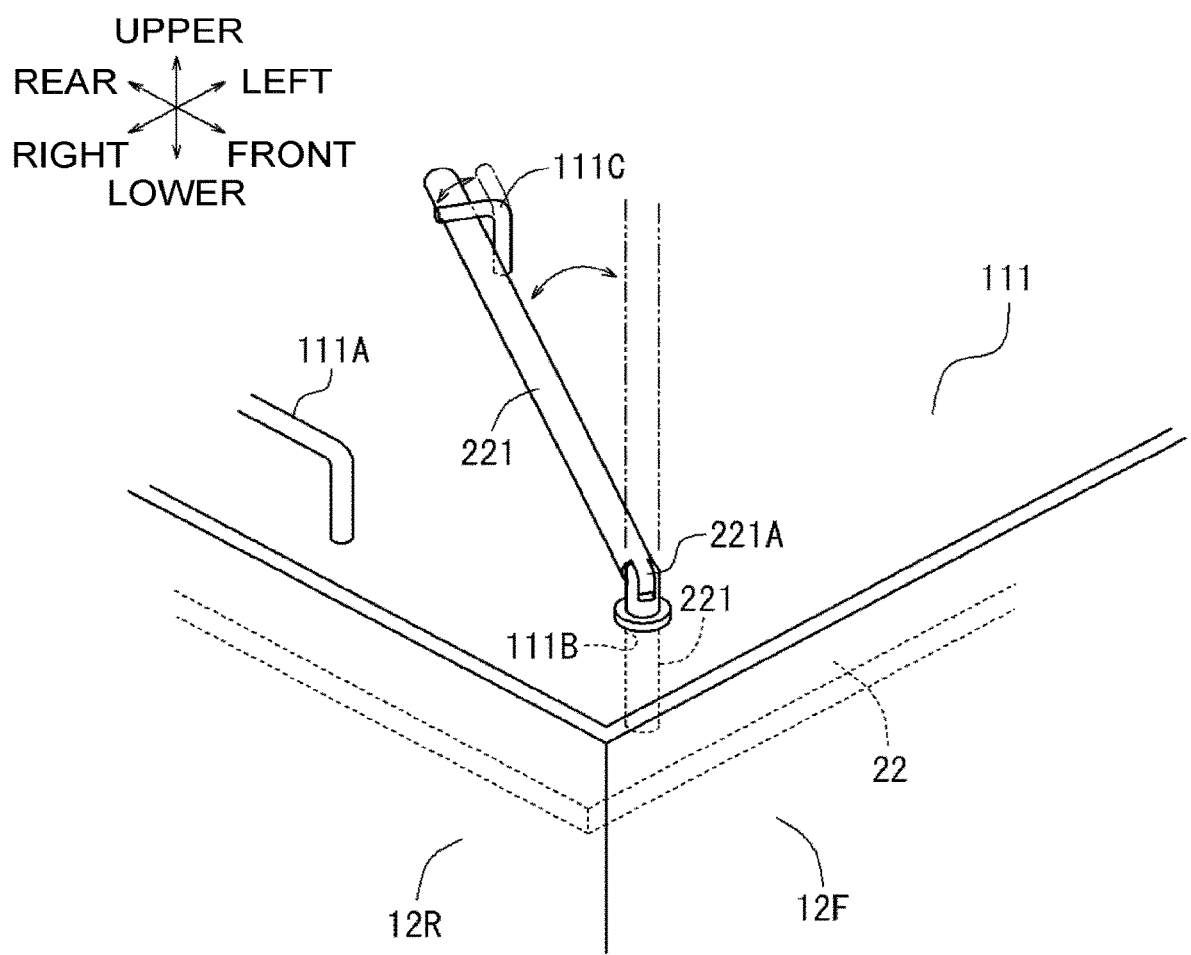
FIG. 6 is a schematic perspective view of a main part of a rearing case in the rearing apparatus according to the embodiment.

First, a configuration of the rearing apparatus 1 according to an embodiment of the present disclosure will be described with reference to FIGS. 1 to 6. FIG. 1 is a schematic perspective view of the rearing apparatus 1. FIG. 2 is a cross-sectional view taken along a line II-II in FIG. 1. FIG. 3 is a cross-sectional view taken along a line in FIG. 2. FIG. 4 is an enlarged view of a portion IV in FIG. 3. FIG. 5 is an explanatory diagram showing a method for using the rearing apparatus 1, and is a schematic cross-sectional view of the rearing apparatus 1. FIG. 6 is a schematic perspective view of a main part of the rearing case 10 in the rearing apparatus 1.

As shown in FIGS. 1 and 2, the rearing apparatus 1 includes a rearing case 10, a belt conveyor 30, a housing 50 (shown by a two-dot chain line in FIG. 1), and the like. Here, the rearing case 10, the belt conveyor 30, and the like are held by the housing 50 that surrounds the rearing case 10, the belt conveyor 30, and the like. The rearing case 10 is provided on the belt 32 of the belt conveyor 30. As shown in FIG. 2, in the rearing case 10, the cricket 500 (the organism) is reared inside, and a bottom portion of the rearing case 10 is open. An opening of the bottom portion of the rearing case 10 is closed by the belt 32 of the belt conveyor 30.

As shown in FIG. 1, the rearing case 10 is formed in a box shape, and includes a ceiling portion 11 that closes an upper surface and a side wall portion 12 that surrounds a side surface. As described above, the bottom portion of the rearing case 10 surrounded by the side wall portion 12 is open, and is closed by the belt 32 of the belt conveyor 30. That is, as shown in FIG. 2, a part of the belt 32 of the belt conveyor 30 is a floor surface 13 of the rearing case 10. As shown in FIG. 2, in the rearing case 10, a plurality of perching members 21 whose upper end portions are held by the ceiling portion 11, and a separating member 22 that has a perching member through hole 22A and that can be moved along the perching member 21 are provided. The perching member 21 is inserted through the perching member through hole 22A. The rearing case 10 is formed of, for example, a resin. The rearing case 10 has, for example, a height of approximately 400 [mm], a width in the left-right direction of approximately 700 [mm], and a depth in the front-rear direction of approximately 400 [mm].

As shown in FIGS. 1 and 2, the ceiling portion 11 includes two plate-shaped ceiling plates 111 placed on the side wall portion 12. Each ceiling plate 111 includes two handles 111A (see FIG. 1), two rod-shaped member insertion holes 111B (see FIG. 2), and two rod-shaped member holding portions 111C. As shown in FIG. 2, each ceiling plate 111 holds the plurality of plate-shaped perching members 21.

As shown in FIG. 1, the handle 111A is provided at each of a left side end portion and a right side end portion of the ceiling plate 111. The user can grip the handle 111A and lift the ceiling plate 111 (the ceiling portion 11) to remove, from the rearing case 10, the ceiling plate 111 (the ceiling portion 11) and a plurality of perching members 21 to be described later held by the ceiling plate 111.

The rod-shaped member insertion hole 111B will be described in detail later with reference to FIG. 6, and as shown in FIG. 2, the rod-shaped member insertion hole 111B is a through hole through which a rod-shaped member 221 extending upward from the separating member 22 is inserted. The rod-shaped member holding portion 111C will be described in detail later with reference to FIG. 6. As shown in FIGS. 1 and 6, the rod-shaped member holding portion 111C is formed in an inverted L shape in a side view, and a lower side of the rod-shaped member holding portion 111C is rotatably (see FIG. 6) held by the ceiling plate 111. As shown in FIGS. 1 and 2, the rod-shaped member 221 protrudes upward from the rod-shaped member insertion hole 111B and is bent when the cricket 500 (the organism) is reared, and is held at a distal end side thereof by the rod-shaped member holding portion 111C. Here, as shown in FIG. 1, the rod-shaped member holding portion 111C holds the rod-shaped member 221 by pressing the rod-shaped member 221 from above.

As shown in FIGS. 1 and 2, the side wall portion 12 surrounds a side surface of the rearing case 10, and includes a front wall portion 12F on a front side, a rear wall portion 12B (see FIG. 3) on a rear side, a left wall portion 12L (see FIG. 2) on a left side, and a right wall portion 12R on a right side. As shown in FIG. 1, the front wall portion 12F includes a transparent window portion 12F1, and similarly, the rear wall portion 12B (see FIG. 3) also includes a transparent window portion (not shown). A lower portion of the front wall portion 12F and the belt 32 of the belt conveyor 30 are closed, and similarly, a lower portion of the rear wall portion 12B (see FIG. 3) and the belt 32 of the belt conveyor 30 are also closed.

As shown in FIG. 1, the right wall portion 12R includes a transparent window portion 12R1 and a door portion 12R2 below the window portion 12R1. As shown in FIGS. 1 and 2, the door portion 12R2 can be opened and closed by rotating around an upper side, and a brush 12R2A is provided on a lower side of the door portion 12R2. When the door portion 12R2 is closed, a gap between the right wall portion 12R and the belt 32 of the belt conveyor 30 is blocked by the brush 12R2A such that the cricket 500 does not escape. As shown in FIG. 2, similarly to the right wall portion 12R, the left wall portion 12L includes a transparent window portion (not shown) and a door portion 12L2 below the window portion. Similarly to the door portion 12R2 of the right wall portion 12R, the door portion 12L2 can be opened and closed by rotating around an upper side, and the brush 12L2A is provided on a lower side of the door portion 12L2. As described above, when the door portion 12L2 of the front wall portion 12F and the door portion 12R2 of the rear wall portion 12B (see FIG. 3) are closed, a gap between the right wall portion 12R and the belt 32 and a gap between the left wall portion 12L and the belt 32 are blocked by the brush 12R2A and the brush 12L2A. Accordingly, the cricket 500 is prevented from escaping through between the side wall portion 12 and the belt 32 of the belt conveyor 30.

As shown in FIG. 2, an upper end portion of the perching member 21 is held by the ceiling plate 111. As shown in FIGS. 2 and 3, a plurality of perching members 21 are provided in the rearing case 10. As shown in FIG. 3, the perching member 21 is formed in a square wave shape in which a cross section as viewed from an upper surface extends in the front-rear direction, and the plurality of perching members 21 are provided in the rearing case 10 at an interval. Here, a length of one side of a square wave of the perching member 21 having a square wave shape cross section is, for example, approximately 20 [mm] such that the cricket 500 easily enters irregularities of the square wave. A distance between the two perching members 21 adjacent to each other in the left-right direction is, for example, approximately 20 [mm]. A gap between the perching member 21 and the floor surface 13 of the rearing case 10 is set to such an extent that the cricket 500 can pass through the gap, and is, for example, 1 [mm] to 20 [mm]. As a material of the perching member 21, metal including iron such as stainless steel, aluminum or galvanized steel plate, wood, paper, resin, or the like is appropriately used.

As shown in FIG. 4, the perching member 21 is formed with a large number of pores 21A penetrating the perching member 21 over an entire surface of the perching member 21 such that the pores 21A serve as a scaffold for the cricket 500. Accordingly, the perching member 21 is held in the rearing case 10, and can perch the cricket 500 (the organism) to be reared. The pore 21A is, for example, a through hole having a diameter of approximately 1 [mm], and an interval between the pore 21A and the adjacent pore 21A is, for example, approximately 1 [mm]. The shape, the number, and the interval of the pores 21A of the perching member 21 can be appropriately changed, and it is sufficient that the cricket 500 can perch at the perching member 21 using the pores 21A as a scaffold. The perching member 21 may be formed of a punching metal, or may be formed of a wire mesh such as an expanded metal.

As shown in FIG. 2, the separating member 22 is provided below each of the two ceiling plates 111 of the rearing case 10. The separating member 22 is formed in a plate shape, has a plurality of perching member through holes 22A (see FIGS. 2 and 4) through which the perching member 21 is inserted, and is attached with a lower end portion (see FIGS. 2 and 6) of the rod-shaped member 221. As shown in FIG. 4, the perching member through hole 22A is provided with a seal member 22AA that fills a gap between the separating member 22 and the perching member 21. That is, as shown in FIG. 4, the separating member 22 includes the seal member 22AA that fills the gap between the separating member 22 and the perching member 21.

Here, the seal member 22AA is movable without fixing the perching member 21 to the separating member 22. Therefore, the separating member 22 can be moved along the perching member 21. The seal member 22AA is formed of, for example, a rubber-shaped resin having elasticity. As long as the seal member 22AA can fill the gap between the separating member 22 and the perching member 21, the seal member 22AA may be formed of rubber or elastomer having elasticity as a resin, may be formed of a resin having low elasticity, or may be formed of a sponge or a brush.

As shown in FIGS. 3 and 6, the rod-shaped member 221 includes a lower end portion held at a corner portion (a rear right portion of the separating member 22 or a front left portion of the separating member 22) of the separating member 22, extends upward from the corner portion of the separating member 22, and includes a hinge 221A (see FIG. 6). As shown in FIGS. 1, 2, and 6, each of the rod-shaped members 221 extends from the separating member 22 to the outside (upper) of the rearing case 10, and is inserted into the rod-shaped member insertion hole 111B of the ceiling plate 111. The rod-shaped member 221 is a moving member that moves the separating member 22. The user can move the separating member 22 in the upper-lower direction by gripping a portion (see FIG. 5) protruding upward from the ceiling plate 111 of the rod-shaped member 221, and can more reliably move the separating member 22 by the rod-shaped member 221.

The separating member 22 is positioned at a rearing position S1 on an upper side when the cricket 500 (the organism) is reared. The hinge 221A of the rod-shaped member 221 is provided on a lower side of the rod-shaped member 221. When the separating member 22 is at the rearing position S1, as described below, the rod-shaped member 221 can be folded by the hinge 221A and held by the ceiling plate 111 (the ceiling portion 11). That is, as shown in FIG. 6, the rod-shaped member 221 is bent by the hinge 221A, and the rod-shaped member holding portion 111C is rotated such that a distal end portion of the rod-shaped member holding portion 111C of the ceiling plate 111 overlaps the rod-shaped member 221. Accordingly, as shown in FIGS. 1 and 6, the distal end portion of the rod-shaped member 221 is supported by the rod-shaped member holding portion 111C, and the rod-shaped member 221 is prevented from extending by the hinge 221A. Accordingly, the rod-shaped member 221 (the moving member) is held in a state of being folded by the hinge 221A. As a result, the rod-shaped member 221 holds the separating member 22 at the rearing position S1. As described above, when the cricket 500 (the organism) is reared, the rod-shaped member 221 is folded by the hinge 221A without straightly protruding upward from the ceiling portion 11 (the ceiling plate 111) of the rearing case 10.

Then, as shown in FIG. 6, when the rod-shaped member holding portion 111C is rotated such that the rod-shaped member holding portion 111C does not overlap the rod-shaped member 221, the bent rod-shaped member 221 can be extended straightly. Here, when the user grips the rod-shaped member 221, straightly extends the rod-shaped member 221, and further pushes down the rod-shaped member 221 downward, as shown in FIG. 5, the separating member 22 holding a lower end of the rod-shaped member 221 is pushed down by the rod-shaped member 221. As will be described in detail later, as shown in FIG. 5, a state in which the separating member 22 is pressed down to the bottom portion of the rearing case 10 is referred to as a collection position S2 of the separating member 22 at which the separating member 22 is positioned when the cricket 500 (the organism) is collected.

When the user grips the rod-shaped member 221 and moves the rod-shaped member 221 in the upper-lower direction, the separating member 22 holding the rod-shaped member 221 also moves in the upper-lower direction. The user can move the rod-shaped member 221 in the upper-lower direction and move the separating member 22 between the rearing position S1 on the upper side and the collection position S2 on a lower side. As described above, the separating member 22 includes the moving member (the rod-shaped member 221) that reciprocates between the rearing position S1 at which the separating member 22 is positioned when the cricket 500 (the organism) is reared and the collection position S2 at which the separating member 22 is positioned when the cricket 500 (the organism) is collected. The moving member (the rod-shaped member 221) is a rod-shaped member 221 that can be folded at the rearing position S1.

As shown in FIGS. 1 and 2, the belt conveyor 30 is provided at the bottom portion of the rearing case 10, in other words, is provided at the bottom portion of a space in the rearing case 10. The belt conveyor 30 includes a pair of rollers 31, the belt 32 stretched between the pair of rollers 31, and a belt cleaning unit 33 configured to clean the belt 32. The belt conveyor 30 is provided with a water supply apparatus 40 configured to supply water to the cricket 500.

As shown in FIG. 2, the roller 31 is rotated by a motor (not shown). A rotation direction of the roller 31 is indicated by an arrow in FIG. 2. As a material of the roller 31, for example, rubber is used. As the roller 31 rotates, the belt 32 rotates. In this manner, the belt conveyor 30 is of an electric type in which the roller 31 is rotated by a motor (not shown) and a power source (not shown). As the power source of the motor (not shown), for example, a receptacle to which electricity is supplied from a power plant, a primary battery such as an alkaline battery, a rechargeable secondary battery such as a lithium ion secondary battery or a lead storage battery, or a lithium ion capacitor is used.

As shown in FIG. 2, the belt 32 is provided at the bottom portion of the space in the rearing case 10, and a part of the belt 32 is the floor surface 13 of the rearing case 10. When the belt 32 rotates in a direction of the arrow shown in FIG. 2 by rotating the roller 31, the floor surface 13 of the rearing case 10, which is a part of the belt 32, moves from left to right. Accordingly, deposits (for example, excrement, shells, carcasses, and leftover food) accumulated on the floor surface 13 of the rearing case 10 are carried out from the inside of the rearing case 10 to the outside. Here, as described above, the gap between the left wall portion 12L and the belt 32 and the gap between the right wall portion 12R and the belt 32 are blocked by the brush 12L2A and the brush 12R2A. Accordingly, even if the belt 32 rotates and the floor surface 13 moves from left to right, the cricket 500 is prevented from escaping through the gap between the left wall portion 12L and the belt 32 and the gap between the right wall portion 12R and the belt 32.

As shown in FIG. 2, the belt cleaning unit 33 includes a scraper 331 that abuts against the belt 32 on a lower side of the left roller 31, and a tray 332 that is provided below the scraper 331 and that surrounds the left roller 31 and the scraper 331.

The scraper 331 is formed in a spatula shape having a sharp upper end, a thickness of which decreases toward an upper end side abutting against the belt 32. The upper end portion formed in the spatula shape of the scraper 331 abuts against the belt 32 from a front end to a rear end of the belt 32. A lower side of the scraper 331 is held by the housing 50. The sharp upper end portion of the scraper 331 abuts against the belt 32 on a lower side of the right roller 31, so that an attached matter adhering to the belt 32 is scraped off from the belt 32 and is further stored in the tray 332 placed below the scraper 331.

As described above, when the belt 32, which is partly the floor surface 13, rotates, the deposits deposited on the floor surface 13 of the rearing case 10 are conveyed to a right side of the rearing case 10 by the moving belt 32 (the floor surface 13), and falls into the tray 332 from above the belt 32 on a left side of the right roller 31. Further, the attached matter adhering to the belt 32 without falling off the belt 32 is scraped off by the scraper 331, and the belt 32 is cleaned.

As shown in FIGS. 1 and 2, the water supply apparatus 40 includes the water supply band 41 that is wound around an outer side of the belt 32 and that extends along a circumferential direction of the belt 32, a water supply device 42 configured to supply water to the water supply band 41, and a water supply band cleaning unit 43 configured to clean the water supply band 41.

As shown in FIGS. 1 and 2, the water supply band 41 is single-wound around the outer side of the belt 32 and extends along the circumferential direction of the belt 32, and is formed in a band shape having a rectangular cross section. The water supply band 41 is formed of a water-retaining material capable of retaining water therein. Here, the water supply band 41 is a water supply member capable of retaining water therein and capable of supplying the retained water to the cricket 500 (the organism). In other words, the belt 32 includes a water supply member (the water supply band 41) capable of retaining water therein and capable of supplying the retained water to the cricket 500 (the organism). The material of the water supply band 41 may be any water-retaining material capable of retaining water therein, and for example, a mixture of one or more of a water-absorbent polymer material, a cloth such as a non-woven fabric, cotton, pulp, and a sponge is used.

As shown in FIGS. 1 and 2, the water supply device 42 is provided on a left end side of the belt 32 and is held by the housing 50. As shown in FIG. 2, the water supply device 42 includes a water tank 421 in which water is stored, a water supply pipe 422 having one end connected to the water tank 421 and the other end opening on the water supply band 41, and a pump 423 provided in the water supply pipe and configured to convey water. As the pump 423, an electric pump that is driven by electricity from the above-described power supply and that is configured to convey water is used. A manual pump configured to manually convey water may be used as the pump 423. When the pump 423 conveys water, the water stored in the water tank 421 drops onto the water supply band 41, and water permeates into the water supply band 41. Accordingly, water is retained in a part of the water supply band 41.

As shown in FIG. 2, the water supply band cleaning unit 43 is provided on a lower side with respect to the right roller 31 and on a left side of the scraper 331, and is held by the housing 50. The water supply band cleaning unit 43 includes a cleaning liquid tank 431 in which a cleaning liquid 431L is stored, a cleaning roller 432 that is provided on an upper side of the belt 32 and that abuts against the belt 32, and the like. The cleaning liquid 431L is appropriately supplied to the cleaning liquid tank 431 and is replaced. As the cleaning liquid 431L, a liquid harmless to the cricket 500 (the organism) is preferable.

The cleaning roller 432 is provided on the upper side of the belt 32 and abuts against the belt 32 on a lower side of the cleaning roller 432. Accordingly, around the cleaning roller 432, the belt 32 is pressed downward by the cleaning roller 432. A position of the cleaning roller 432 is set to such a position that the belt 32 pushed down by the cleaning roller 432 is immersed in the cleaning liquid 431L stored in the cleaning liquid tank 431 and is cleaned. In this way, the water supply band cleaning unit 43 can clean the belt 32 by immersing the belt 32 in the cleaning liquid 431L in the cleaning liquid tank 431.

As described above, the water supply apparatus 40 can be used to supply water to the cricket 500 (the organism) to clean the water supply band 41 as follows. As shown in FIG. 2, the water in the water tank 421 is conveyed to the pump 423 of the water supply device 42, and the water is dropped onto the water supply band 41. Accordingly, in a portion of the water supply band 41 onto which the water is dropped, water permeates into an inside of the portion, and water is retained inside. When the belt 32 further rotates, the portion of the water supply band 41 that retains water therein moves together with the belt 32 into the space in the rearing case 10. Then, the cricket 500 can obtain water from the water supply band 41 by being brought into contact with the portion of the water supply band 41 that retains water therein.

Then, when the belt 32 further rotates, the water supply band 41 is cleaned as follows. First, the attached matter on the water supply band 41 is scraped off by the scraper 331 similarly to the attached matter on the belt 32, and is stored in the tray 332. Further, as the belt 32 is rotated, the water supply band 41 is cleaned by being immersed in the cleaning liquid 431L at the water supply band cleaning unit 43. The water supply band 41 (the water supply member) is provided on the belt 32 of the belt conveyor 30. In other words, the belt 32 of the belt conveyor 30 includes the water supply band 41 (the water supply member) capable of retaining water therein and capable of supplying the retained water to the cricket 500 (the organism).

[Use Method and Effect (FIGS. 1 to 7) of Rearing Apparatus 1 According to Embodiment]

Next, two use methods which are (A) a use method in rearing the cricket 500 (the organism), and (B) a use method in collecting the cricket 500 (the organism) will be described together with an effect. A temperature and humidity in the rearing case 10, an amount of light reaching the inside of the rearing case 10 depending on an illumination, and the like are appropriately adjusted.

First, (A) the use method in rearing the cricket 500 (the organism) will be described together with the effect. FIG. 2 is a schematic cross-sectional view of the rearing apparatus 1 in rearing the cricket 500 (the organism). As shown in FIG. 2, in rearing, the door portion 12R2 of the right wall portion 12R and the door portion 12L2 of the left wall portion 12L are kept in a closed state. A feed of the cricket 500 (the organism) is appropriately given according to various methods. For example, a powdered feed is placed on the left end side (the left side with respect to the rearing case 10) of the belt 32, and the belt 32 is rotated to carry the feed to the floor surface 13 in the rearing case 10 to feed the cricket 500. In addition, for example, a box in which a feed is placed is provided in the rearing case 10 such that the cricket 500 can eat the feed, and the cricket 500 is fed.

As shown in FIG. 2, the separating member 22 is located at the rearing position S1 in rearing. As described above with reference to FIG. 6, the separating member 22 is held at the rearing position S1 by the rod-shaped member 221 whose lower end portion is held by the separating member 22. That is, the rod-shaped member 221 is folded by the hinge 221A, and the rod-shaped member 221 is further held by the rod-shaped member holding portion 111C. Accordingly, the rod-shaped member 221 is held by the rod-shaped member holding portion 111C, and the separating member 22 holding the rod-shaped member 221 is held at the rearing position S1 by the rod-shaped member 221.

The moving member of the rearing apparatus 1 is a rod-shaped member 221 that can be folded at the rearing position S1. Accordingly, as described above, it is more reliable and easier to move the separating member 22 in the upper-lower direction. By folding the rod-shaped member 221, it is possible to prevent the moving member (the rod-shaped member 221) from protruding from the rearing case 10 and becoming bulky. More specifically, the rod-shaped member 221 is folded by the hinge 221A, so that the rod-shaped member 221 does not straightly extend onto the rearing case 10 in rearing. Therefore, by folding the rod-shaped member 221, it is possible to prevent the moving member (the rod-shaped member 221) from straightly protruding from the rearing case 10 and becoming bulky.

As shown in FIG. 2, the separating member 22 is held at the rearing position S1 on the upper side of the rearing case 10, and as shown in FIG. 3, a plurality of perching members 21 are inserted into the perching member through hole 22A. As described above with reference to FIG. 3, the perching member 21 is formed in a square wave shape in which the cross section viewed from the upper surface extends in the front-rear direction. As described above with reference to FIG. 4, the cricket 500 can be perched at the perching member 21 using a large number of pores 21A formed in the perching member 21 as a scaffold. Here, since the cross section of the perching member 21 has a square wave shape having a large number of irregularities, the cricket 500 perched at the perching member 21 is less likely to be viewed from the surrounding cricket 500. Accordingly, the perching member 21 has a function as a hideout for the cricket 500. Further, since the number of the perching members 21 provided in the rearing apparatus 1 is plural, a relatively large quantity of crickets 500 (organisms) can be perched by the perching member 21 and reared.

The rearing apparatus 1 includes the perching member 21 and the separating member 22. The cricket 500 (the organism) reared in the rearing case 10 can move and perch at the perching member 21. In this way, the cricket 500 (the organism) can perch at the perching member 21, so that the rearing apparatus 1 can rear the cricket 500 (the organism) in an environment more suitable for growth.

As shown in FIG. 2, the cricket 500, which moves from the floor surface 13 (the belt 32) of the rearing case 10 to the perching member 21 and further climbs on the perching member 21, is more reliably prevented from climbing above the rearing position S1 of the separating member 22 by the seal member 22AA (see FIG. 4) that fills the gap between the separating member 22 and the perching member 21. Accordingly, the cricket 500 is more reliably reared in a space below the separating member 22 in rearing.

As described above with reference to FIG. 2, the rearing apparatus 1 includes the belt conveyor 30, and a part of the belt 32 of the belt conveyor 30 is the floor surface 13 of the rearing case 10. In rearing, the belt 32 is appropriately rotated by rotating the roller 31 of the belt conveyor 30 in a direction of an arrow in FIG. 2. When the belt 32 rotates, the floor surface 13, which is a part of the belt 32, moves to the right. Accordingly, when the belt 32 rotates, the deposits (for example, excrement, shells, carcasses, and leftover food) deposited on the floor surface 13 of the rearing case 10 are conveyed to the right side of the rearing case 10 together with the floor surface 13, and further fall into the tray 332 from above the belt 32 on the right side of the right roller 31. The attached matter adhering to the belt 32 without dropping from the belt 32 is scraped off by the scraper 331 and falls into the tray 332. In this way, the deposits deposited on the floor surface of the rearing case 10 can be dropped into the tray 332 simply by rotating the belt 32.

As described above, the rearing apparatus 1 includes the belt conveyor 30 provided at the bottom portion of the space in the rearing case 10. The belt conveyor 30 can more easily discharge the deposits (for example, excrement, shells, carcasses, and leftover food) deposited on the bottom portion of the space in the rearing case 10 from the inside of the rearing case 10 to the outside. Here, the deposits (for example, excrement, shells, carcasses, and leftover food) deposited on the floor surface 13 (the belt 32) of the rearing case 10 are cleaned only by rotating the belt 32, so that good hygiene can be maintained more easily in the rearing case 10.

As described above with reference to FIGS. 1 and 2, the belt 32 of the belt conveyor 30 includes the water supply band 41 (the water supply member) capable of retaining water therein and capable of supplying the retained water to the cricket 500 (the organism). As described above, the water supply band 41 is wound on the belt 32 of the belt conveyor 30. Water is dropped onto the water supply band 41 from the water supply device 42, and the portion of the water supply zone 41 onto which water is dropped retains water. In this way, water is supplied to the water supply band 41. Then, the belt 32 is rotated to move the portion of the water supply band 41 retaining water therein into the rearing case 10. Accordingly, the cricket 500 comes into contact with the portion of the water supply band 41 retaining water therein to obtain water.

As described above, the rearing apparatus 1 includes the water supply band 41 (the water supply member) capable of retaining water inside the belt 32 of the belt conveyor 30 and capable of supplying the retained water to the cricket 500 (the organism). Accordingly, water can be supplied to the cricket 500 (the organism) as long as the water supply band 41 (the water supply member) is used. Therefore, it is easy to apply water to the cricket 500 (the organism). Here, clean water can be supplied from the water supply device 42 to the water supply band 41. Therefore, the cricket 500 can ingest hygienic water.

A portion of the water supply band 41 of the belt 32 retaining water therein is carried to the outside (the left side) of the rearing case 10 by the rotation of the belt 32, and is further cleaned by the water supply band cleaning unit 43 as described above. In this way, since the portion of the water supply band 41 of the belt 32 retaining water therein is used for supplying water to the cricket 500 and then cleaned by the water supply band cleaning unit 43, the inside of the rearing case 10 can be kept hygienic.

Here, the water can be supplied to the cricket 500 simply by supplying water to the water tank in the water supply device 42 and rotating the belt 32. Therefore, water can be supplied to the cricket 500 more easily. Further, dirt of the water supply band 41 is collected in the cleaning liquid 431L in the water supply band cleaning unit 43, and the water supply band 41 can be continuously cleaned as long as the cleaning liquid 431L is replaced. Accordingly, maintenance of the water supply apparatus 40 becomes easier.

Next, (B) the use method in collecting the cricket 500 (the organism) will be described together with an effect. In collection, first, as shown in FIG. 6, the rod-shaped member holding portion 111C that presses the rod-shaped member 221 from above is rotated, and the rod-shaped member holding portion 111C is moved to a position away from the rod-shaped member 221 such that the rod-shaped member holding portion 111C does not overlap the rod-shaped member 221. Then, the rod-shaped member 221 bent by the hinge 221A is extended straightly. Further, the user grips the rod-shaped member 221 and pushes down the rod-shaped member 221 extending straightly downward. Accordingly, as shown in FIG. 5, the separating member 22 that holds the lower end of the rod-shaped member 221 is pushed down by the rod-shaped member 221. The rearing apparatus 1 includes the rod-shaped member 221 as a moving member, and the user can grip the rod-shaped member 221 and push down the separating member 22 from the rearing position S1 in rearing to the collection position S2 in collection as shown in FIG. 5. Since the separating member 22 can be held at the rearing position S1 only by providing the rod member holding portion 111C, in the rearing apparatus 1, a mechanism that holds the separating member 22 at the rearing position S1 has a simple configuration in which the rod-shaped member insertion hole 111B and the rod-shaped member holding portion 111C are provided.

Here, when the separation member 22 is pushed down from the rearing position S1 to the collection position S2, the separating member 22 moves along the perching member 21. The cricket 500 is perched at the perching member 21 in rearing, and as shown in FIG. 4, the gap between the separating member 22 and the perching member 21 is filled by the seal member 22AA. Therefore, as the separating member 22 moves from the rearing position S1 to the collection position S2, the cricket 500 (the organism) perched at the perching member 21 is separated from the perching member 21. In this way, the separating member 22 can separate the cricket 500 (the organism) perched at the perching member 21 from the perching member 21 as the separating member 22 is moved along the perching member 21. Here, the cricket 500 (the organism) can be separated from the perching member 21 without lifting up the ceiling portion 11 (the ceiling plate 111). Therefore, as compared with a case in which the ceiling portion 11 is lifted and the cricket 500 (the organism) is manually separated from the perching member 21, the cricket 500 (the organism) can be separated from the perching member 21 in a smaller space.

Then, as shown in FIG. 5, the cricket 500 (the organism) separated from the perching member 21 is collected at the bottom portion of the rearing case 10. Further, as shown in FIG. 7, when the door portion 12R2 of the right wall portion 12R of the rearing case 10 is opened and the belt 32 of the belt conveyor 30 is rotated, the cricket 500 can be discharged from the door portion 12R2 of the rearing case 10 to the outside of the rearing case 10. In this way, the cricket 500 can be discharged from the door portion 12R2 and collected.

Here, a bag may be placed immediately outside the door portion 12R2, and the cricket 500 discharged from the door portion 12R2 may be put into the bag or the like and collected in the bag.

In (B) the use method in collecting the cricket 500 (the organism) described above, first, as shown in FIG. 5, the user presses down the separating member 22 from the rearing position S1 to the collection position S2. Next, as shown in FIG. 7, in a state in which the door portion 12R2 of the right wall portion 12R of the rearing case 10 is opened, the user rotates the belt 32 of the belt conveyor 30 to discharge the cricket 500 from the door portion 12R2 of the rearing case 10 to the outside to collect the cricket 500. Here, an operation of pressing the separating member 22 from the rearing position S1 to the collection position S2 and an operation of rotating the belt 32 of the belt conveyor 30 and discharging the cricket 500 from the door portion 12R2 of the rearing case 10 to the outside in the state in which the door portion 12R2 of the right wall portion 12R of the rearing case 10 is opened as shown in FIG. 7 may be performed at the same time. If the operations are performed at the same time in this way, by increasing or decreasing a force to push down the separating member 22, it is possible to adjust the number of the crickets 500 separated from the separating member 22 per certain period of time, and thus, it is possible to adjust the number of the crickets 500 separated from the separating member 22 and discharged from the door portion 12R2 per certain period of time. Accordingly, it is possible to prevent the cricket 500 from being discharged to the outside from the door portion 12R2 of the rearing case 10 at once.

The user can also grip the rod-shaped member 221 to pull up the separating member 22 at the collection position S2 from the collection position S2 to the rearing position S1 as shown in FIG. 5. Therefore, the user can grip the rod-shaped member 221 to reciprocally move the separating member 22 between the rearing position S1 and the collection position S2. In other words, the separating member 22 includes the rod-shaped member 221 (the moving member) that reciprocates between the rearing position S1 at which the separating member 22 is positioned when the cricket 500 (the organism) is reared and the collection position S2 at which the separating member 22 is positioned when the cricket 500 (the organism) is collected. By providing the rod-shaped member 221 (the moving member), it is easier to move the separating member 22 along the perching member 21. Therefore, it is easier to separate the cricket 500 (the organism) perched at the perching member 21 from the perching member 21.

As shown in FIG. 4, the rearing apparatus 1 includes the seal member 22AA that fills the gap between the separating member 22 and the perching member 21. The seal member 22AA prevents the cricket 500 (the organism) from passing through the gap between the separating member 22 and the perching member 21. Therefore, by providing the seal member 22AA, the separating member 22 is moved along the perching member 21. Accordingly, the cricket 500 (the organism) perched at the perching member 21 can be more reliably separated when being separated from the perching member 21. Even if the cricket 500 remains without being separated from the perching member 21 by the separating member 22, the cricket 500 is in the rearing case 10 and cannot escape to the outside, and thus it is relatively easy to catch the cricket 500.

The method for using the rearing apparatus 1 has been described above. As described above, the rearing apparatus 1 includes the perching member 21 and the separating member 22. The cricket 500 (the organism) reared in the rearing case 10 can move and perch at the perching member 21. In this way, the cricket 500 (the organism) can perch at the perching member 21, so that the rearing apparatus 1 can rear the cricket 500 (the organism) in an environment more suitable for growth. By moving the separating member 22 along the perching member 21, the cricket 500 (the organism) perched at the perching member 21 can be separated from the perching member 21. Accordingly, it is easier to collect the reared cricket 500 (the organism). Therefore, the rearing apparatus 1 can rear the cricket 500 (the organism) in an environment suitable for growth, and further facilitate the collection of the reared cricket 500 (the organism).

Accordingly, the cricket 500 (the organism) is collected by moving the separating member 22 to the perching member 21 as described above, so that the collection can be performed in a shorter time with less labor as compared with a case of manually performing the collection. In addition, it is easier to collect a large quantity of crickets 500 (organisms) without exception. Further, when the rearing apparatus 1 is used, high-density rearing of the cricket 500 is facilitated, and hygiene management of the rearing environment of the cricket 500 is facilitated. Therefore, when a large number of rearing apparatuses 1 are used, the cricket 500 can be reared in a high density and a large scale in a hygienic environment.

Other Embodiments

The rearing apparatus 1 according to the above-described embodiment is not limited to the above-described configuration, structure, shape, appearance, and the like, and various modifications, additions, and deletions can be made without changing the gist of the present disclosure. For example, in the rearing apparatus 1 according to the embodiment, as described above with reference to FIG. 1, the rearing case 10 includes the window portions such as the window portion 12F1 and the window portion 12R1. Alternatively, the rearing apparatus 1 may not include these window portions, and may include several window portions. For example, the rearing apparatus 1 may not include the door portion 12R2 of the right wall portion 12R. Instead of providing the window portion, the side wall portion 12 of the rearing apparatus 1 may be integrally formed of a transparent glass or a transparent resin. Further, for example, a seal member similar to the seal member 22AA may be used instead of the brush 12L2A provided on the lower side of the door portion 12L2.

In the rearing apparatus 1, the shape, the number, and the interval of the pores 21A of the perching member 21 can be appropriately changed, and it is sufficient that the cricket 500 can perch at the perching member 21 using the pores 21A as a scaffold. For example, a dimple structure or the like may be used in which the shape of the pores 21A is concave. As shown in FIG. 3, the perching member 21 has a square wave shape cross section extending in the front-rear direction as viewed from the upper surface. Alternatively, the cross section only needs to be a plate shape. For example, the cross section of the perching member 21 may have a linear shape, or may have a triangular wave shape, a sawtooth wave shape, a trapezoidal wave shape, a sinusoidal wave shape, or a spiral shape, and can be appropriately changed. Further, the perching member 21 may not be held by the ceiling portion 11, and may be held by the side wall portion 12.

In the rearing apparatus 1, the separating member 22 may not include the seal member 22AA in the gap between the separating member 22 and the perching member 21. Even in a case in which the rearing apparatus 1 does not include the seal member 22AA, when the perching member 21 moves downward along the separating member 22, a part of the crickets 500 (the organisms) perched at the perching member 21 moving downward are reliably separated from the perching member 21 and dropped onto the floor surface 13 (the belt 32) by the perching member 21. Accordingly, it is easier to collect the reared cricket 500 (the organism).

In the rearing apparatus 1, the separating member 22 can be moved in the upper-lower direction. Alternatively, the direction in which the separating member 22 is moved is not limited to the upper-lower direction. As the separating member 22 is moved along the perching member 21, it is sufficient that the cricket 500 (the organism) can be separated from the perching member 21. The direction in which the separating member 22 is moved may be the left-right direction, and may be appropriately changed to a direction from the upper left to the lower right, a direction from the upper right to the lower left, and the like. Therefore, the perching member 21 may be held by the side wall portion 12 or the like.

In the rearing apparatus 1, the separating member 22 is provided with the moving member (the rod-shaped member 221) that reciprocates between the rearing position S1 at which the separating member 22 is positioned when the cricket 500 (the organism) is reared and the collection position S2 at which the separating member 22 is positioned when the cricket 500 (the organism) is collected. However, the moving member (the rod-shaped member 221) may be omitted from the rearing apparatus 1. In the rearing apparatus 1, it is possible to appropriately move the separating member 22 along the perching member 21 without providing the moving member (the rod-shaped member 221). Accordingly, the separating member 22 can separate the cricket 500 (the organism) perched at the perching member 21 from the perching member 21 as the separating member 22 is moved along the perching member 21.

In the rearing apparatus 1, the moving member is the rod-shaped member 221 that can be folded at the rearing position S1. Alternatively, the moving member may not be the rod-shaped member 221. For example, instead of the rod-shaped member 221, a string-shaped member (including a rope, a wire, and the like) that is inserted into the rod-shaped member insertion hole 111B and whose lower end is held by the separating member 22 may be provided in the rearing apparatus 1.

The rearing apparatus 1 includes the belt conveyor 30. Alternatively, the belt conveyor 30 may be omitted from the rearing apparatus 1.

In the rearing apparatus 1, the belt conveyor 30 is of an electric type in which the roller 31 is rotated by a motor (not shown) and a power source (not shown). Alternatively, the belt conveyor 30 may be a manual belt conveyor in which a handle or the like is appropriately provided to rotate the belt 32 together with the roller 31. The pump 423 may be a manual pump.

The rearing apparatus 1 includes the water supply apparatus 40 including the water supply band 41. Alternatively, the water supply apparatus 40 may be omitted from the rearing apparatus 1. As a matter of course, the rearing apparatus 1 includes the water supply member (the water supply band 41). Alternatively, the water supply member (the water supply band 41) may be omitted from the rearing apparatus 1. The rearing apparatus 1 may be provided with a water supply container or the like to supply water to the cricket 500 (the organism).

In the rearing apparatus 1, the water supply band 41 is provided as a water supply member, is formed of a water-retaining material capable of retaining water therein, is single-wound around the outer side of the belt 32 and extends along the circumferential direction of the belt 32, and is formed in a band shape having a rectangular cross section. The water supply band 41 may be wound twice or more around the outer side of the belt 32. It is sufficient that the water supply member is provided on the belt 32, can retain water therein, and can supply the retained water to the cricket 500 (the organism). Therefore, the water supply band 41 may not be formed in a band shape having a rectangular cross section, may have a cross section having a circular shape, an elliptical shape, or a polygonal shape, may have irregularities on the surface thereof, and can be appropriately changed. The water supply member may be formed integrally with the belt 32. The entire belt 32 may be formed of a water-retaining material capable of retaining water therein, and may be a water supply member. Further, at least one water-retaining plate-shaped member capable of retaining water therein may be embedded in a part of the belt 32, and may be replaced with the water supply band 41 as a water supply member.

The present application is based on Japanese Patent Application No. 2020-052445 filed on Mar. 24, 2020, and the contents thereof are incorporated herein by reference.

The invention claimed is:

1. A rearing apparatus for rearing an organism, the rearing apparatus comprising:
   a box-shaped rearing case;
   a perching member that is held in the rearing case for perching the organism; and
   a separating member extending perpendicular to the perching member in the rearing case, the separating member having a plate shape and including a through-hole through which the perching member is inserted,
   wherein the separating member is configured to move in an upper-lower direction within the rearing case to separate the organism perched at the perching member from the perching member by the separating member moving along the perching member through the through-hole.

2. The rearing apparatus according to claim 1,
   wherein the separating member includes a seal member that fills a gap between the through-hole of the separating member and the perching member.

3. The rearing apparatus according to claim 1,
   wherein the separating member includes a moving member configured to reciprocate between a rearing position at which the separating member is positioned when rearing the organism and a collection position at which the separating member is positioned when collecting the organism.

4. The rearing apparatus according to claim 3,
   wherein the moving member is a rod-shaped member configured to fold at the rearing position.

5. The rearing apparatus according to claim 1, further comprising:
   a belt conveyor provided at a bottom portion of a space in the rearing case.

6. The rearing apparatus according to claim 5,
   wherein a belt of the belt conveyor includes a water supply member,
   the water supply member being a water-retaining material that retains water therein and that supplies the retained water to the organism.

7. The rearing apparatus according to claim 1,
wherein the perching member has a square wave shape in which a cross section as viewed from an upper surface extends in a front-rear direction of the rearing case.

8. The rearing apparatus according to claim 7,
wherein the square wave shape extends in the upper-lower direction of the rearing case and the through-hole of the separating member has a corresponding square wave shape along which the separating member moves in the upper-lower direction.

9. The rearing apparatus according to claim 1,
wherein the rearing case includes a ceiling portion that covers a top of the rearing case, the separating members extending in the upper-lower direction from the ceiling portion, and
wherein the rearing apparatus further comprises a rod member attached to the separating member, the rod member extending through the ceiling portion to move the separating member in the upper-lower direction.

10. The rearing apparatus according to claim 9,
wherein the rod member includes a hinge that folds the rod member, and
wherein when the rod member is folded at the hinge, an end of the rod member distal from the separating member is supported by the ceiling portion and the rod member is prevented from extending through the hole.

* * * * *